United States Patent
Barditch et al.

[11] Patent Number: 5,523,235
[45] Date of Patent: Jun. 4, 1996

[54] APPARATUS FOR GROWING MICROORGANISM CULTURES

[75] Inventors: Irving F. Barditch, Baltimore; Maryalice Miller, BelAir, both of Md.

[73] Assignee: The United States of America as represented by the Secretary of the Army, Washington, D.C.

[21] Appl. No.: 293,282

[22] Filed: Aug. 19, 1994

[51] Int. Cl.⁶ ................................. C12M 1/34
[52] U.S. Cl. ................. 435/291.3; 435/288.3; 435/291.4; 435/305.1; 422/102; 220/661; 220/676
[58] Field of Search ............... 435/288.3, 291.3, 435/291.4, 305.1; 220/661, 676; 422/102

[56] References Cited

U.S. PATENT DOCUMENTS

| 5,122,470 | 6/1992 | Banes | 435/240.241 |
| 5,324,657 | 6/1994 | Tanny | 435/240.45 |

*Primary Examiner*—David A. Redding
*Attorney, Agent, or Firm*—Saul Elbaum; Edward L. Stolarun

[57] ABSTRACT

Apparatus for growing cultures of microorganisms comprised of an inert rigid porous member having passageways extending therethrough and structure for bringing liquid in contact with one side of the member. In one species of the invention, the passageways are small enough to prevent microorganisms from flowing through them.

15 Claims, 3 Drawing Sheets

APPARATUS FOR GROWING MICROORGANISM CULTURES

FIELD OF THE INVENTION

The field of the present invention is culturing microorganisms.

BACKGROUND OF THE INVENTION

Cultures of microorganisms are grown among other reasons for purposes of identification, separation, cloning and the accumulation of metabolic products. An early method for growing cultures for one or more of these purposes was to expose the surface of a semi-solid medium known as agar to the bacteria of interest. Because the surface was wet, the bacteria adhered to it, and because nutrients were mixed in the agar, the bacteria in contact with it began to multiply to form a culture. But these localized nutrients were quickly used up so as to limit the amount of growth. Growth was also limited and even altered by the accumulation of metabolic waste in the region of the agar adjacent the colony. Cloning of a particular colony required its identification and removal from the agar by the procedure of carefully accumulating it on a fine probe.

In order to overcome some of the disadvantages of this method of growing pure cultures, vat culture and shaker culture systems were used in which the nutrients and microorganisms were intimately mixed so as to obtain greater growth, but separation of the culture from its metabolic products was obtained by complicated filtering techniques.

BRIEF SUMMARY OF THE INVENTION

By using this invention a culture is provided with a continuous supply of nutrients and a continuous removal of waste products so as to result in greater growth. At the same time the cultures are formed on a surface such that they are isolated and easily identified optically or by phage technique. Most importantly, however, the different colonies can be easily removed by transferring them to absorbent material.

In a preferred embodiment of the invention, nutrient in liquid form is poured into a shallow dish and a plate of inert material having capillary passageways extending from a first to a second surface thereof is mounted on the dish with only the first surface immersed in the liquid. The size of the passageways is such as to permit a flow of nutrient and metabolic waste but to block the flow of the microorganisms of the culture. A passageway having a diameter or maximum lateral dimension of 0.2 microns or less is thought to be appropriate for this purpose. A plate for this purpose can be formed by sintering particles of glass or plastic of appropriate sizes.

Bacteria or other microorganisms to be analyzed are brought into intimate contact with the upper or second surface of the plate and adhere thereto because that surface is wetted by the nutrient liquid drawn thereto by the capillary action. As the colony grows larger on the second or upper surface of the plate, its edges and underside are continuously supplied with nutrient while at the same time metabolic products are drawn away from it by the capillary action of the passageways. The opposite flows of the nutrient and metabolic products occurs because of concentration gradient and diffusion.

In the operation of the invented structure in this manner the colonies are formed at separate locations on the second surface so as to lend themselves to identification by optical or phage techniques. Because the second surface is hard, however, like colonies can be easily removed with blotting paper or the like. Metabolic products mix with the nutrient and purification techniques are used to isolate them. All products are collected. Purification techniques can isolate desirable metabolic products.

In the apparatus described above, there is a porous member having first and second surfaces and means for bringing liquid into contact with one of the surfaces. The porous member, which could be unglazed terra-cotta, is such as to provide capillary action for liquids but prevent the flow of bacteria back into the nutrient source.

In a second apparatus embodying the invention, the porous member is such as to provide capillary action but permit the flow of bacteria or other microorganisms. This apparatus is comprised of a plurality of nested cups. All but the bottom cup are provided with capillary passageways that permit the flow of bacteria in a band intermediate the bottom and rim of the cup. Thus, for example, if raw cabbage is inserted between the cups and the cups are filled with a salt solution and lactobacillus "starter" culture, the culture and salt solution diffuse through the cups and fermentation proceeds. The liquid medium will pass via the passageways in successive cups so as to be collected in the bottom of the top cup and cause the fermented cabbage to have the acidic taste of what is known as sauerkraut. When the level in the top cup reaches the band of openings it passes through them. Cabbage contains water. During the fermentation process it loses water, the volume of liquid medium increases to the overflow holes in the top of the cup and flows through the holes to the bottom reservoir and can be collected for use if desired.

A third apparatus, that is a variation of the second, is comprised of a single cup having capillary passageways in a band intermediate its bottom and its rim. If the cup is an ordinary terra cotta flower pot, a plastic liner is mounted in its bottom so as to seal the hole that is usually therein. A tube is provided for introducing nutrients to the bottom of the cup or to selectively withdraw liquid containing different substances that may be at different levels.

BRIEF DESCRIPTION OF THE DRAWINGS

Various embodiments of the invention are described below with reference to the drawings, in which like items are indicated by the same reference designation, wherein.

DETAILED DESCRIPTION OF THE INVENTION

Figure 1A:
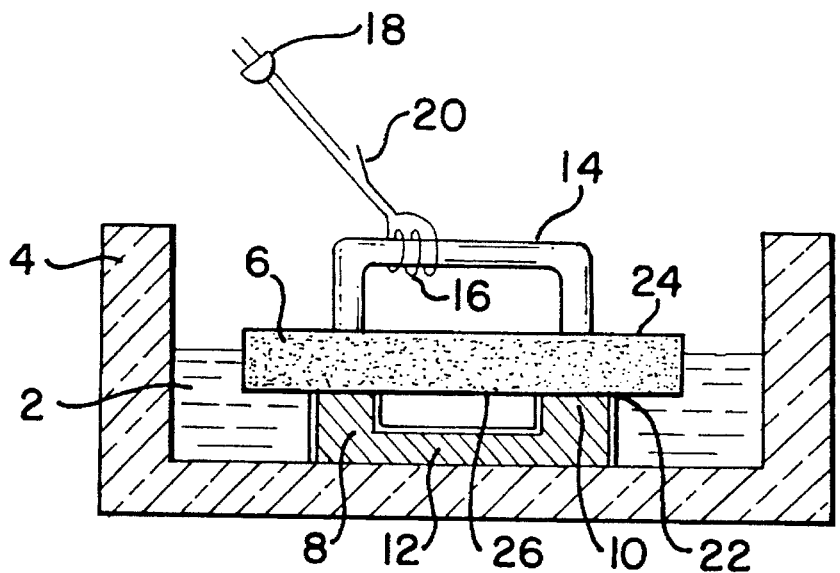
FIG. 1A is a cross-section 1A, 1A of FIG. 1B showing a preferred specie of the invention in which cultures are grown on a porous plate.

In FIG. 1 a liquid nutrient 2 is contained in a glass dish 4 such as a petri dish, and a porous plate 6 is mounted in the dish 4 so that a portion thereof is immersed in the nutrient 2. Although the porous plate 6 may be mounted in other ways, it is shown as being supported by spacer bars 8 and 10 that can be magnetized and are joined at their bottoms by a member 12. In order to facilitate mounting the plate 6 in the dish 4 and removing it therefrom, an electromagnetic U-shaped handle 14 is provided. It is connected to a plug 18 via a switch 20 so that when the plug 18 is inserted in a suitable power jack and the switch 20 is closed, magnetic flux flows through the handle 14. By placing the ends of the "U" in contact with the top of the plate 6 and in registration with the bars 8 and 10, the flux flows through the bars 8 and 10 and the member 12 so as to establish a magnetic force between them and the handle 14 that can be turned on or off by the switch 20. The magnetizable bars 8 and 10 and the member 12 are, if necessary, coated with a film 22 to prevent contamination of the nutrient 2.

The porous plate 6 can be formed by sintered glass or plastic particles or may be made of terra cotta. It contains passageways, not shown, extending from its top surface 24 to its bottom surface 26 that are of such diameter, if cylindrical, as to prevent passage of bacteria, 0.2 microns, for example, while providing capillary attraction for the nutrient 2. The passageways need not be cylindrical, as, for example, when they lie between sintered particles. In such case, the largest dimensions perpendicular or transverse to their length is 0.2 microns or less. Preferably the plate 6 has a porosity of 90%. Thus, when the top surface 24 is exposed to microorganisms, they stick to it and start feeding on the nutrient 2 that is between them and the top surface 24 as well as around them on that surface. Metabolic products secreted by the organisms can escape via the capillary passageways so as not to inhibit or alter the growth of the colony.

Figure 1B:
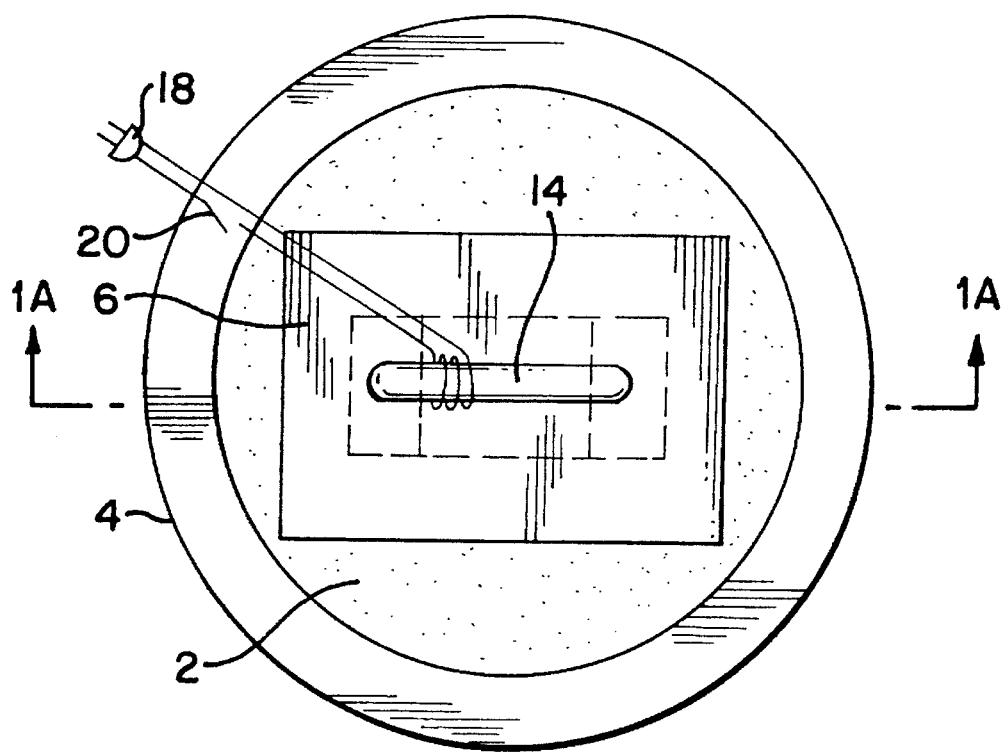
FIG. 1B is a top view of the specie of FIG. 1.

An important application for the apparatus of FIGS. 1A and 1B is the evaluation of the efficiency of filters used in gas masks and elsewhere. Air containing submicron particles of $T_2$-PHAGE virus that attacks *E. coli* is drawn through the filter and directed to the surface 24 of the plate 6. Previously, *E. coli* is grown on the surface 24 so that the concentration of $T_2$-PHAGE can be determined by the amount of *E. coli* that is killed.

Figure 2A:
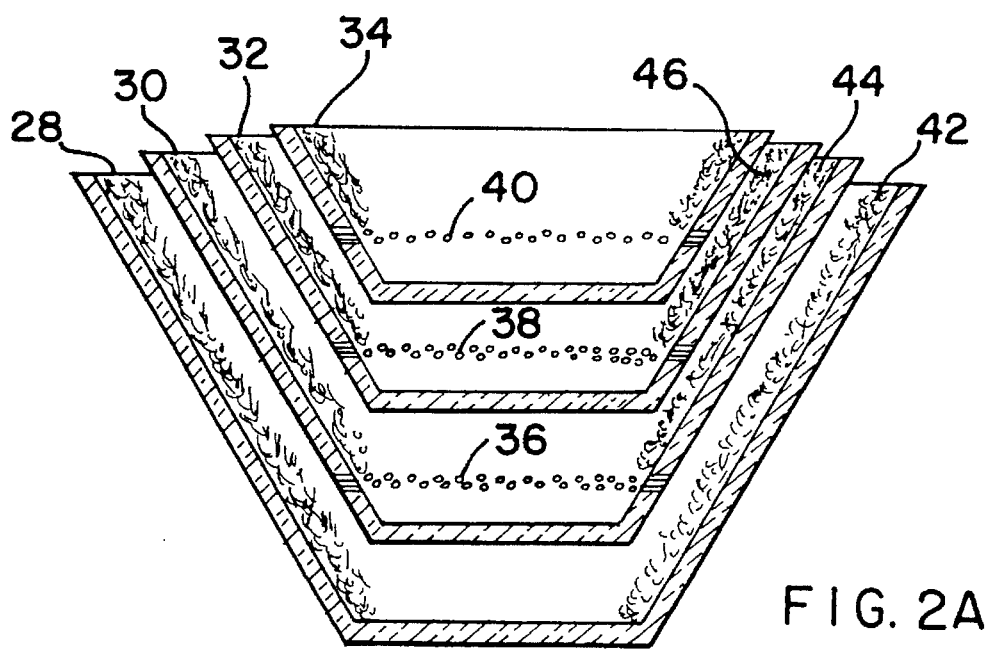
FIG. 2A is a cross-section of a specie of the invention in which cultures are grown in nested cups.
Figure 2B:
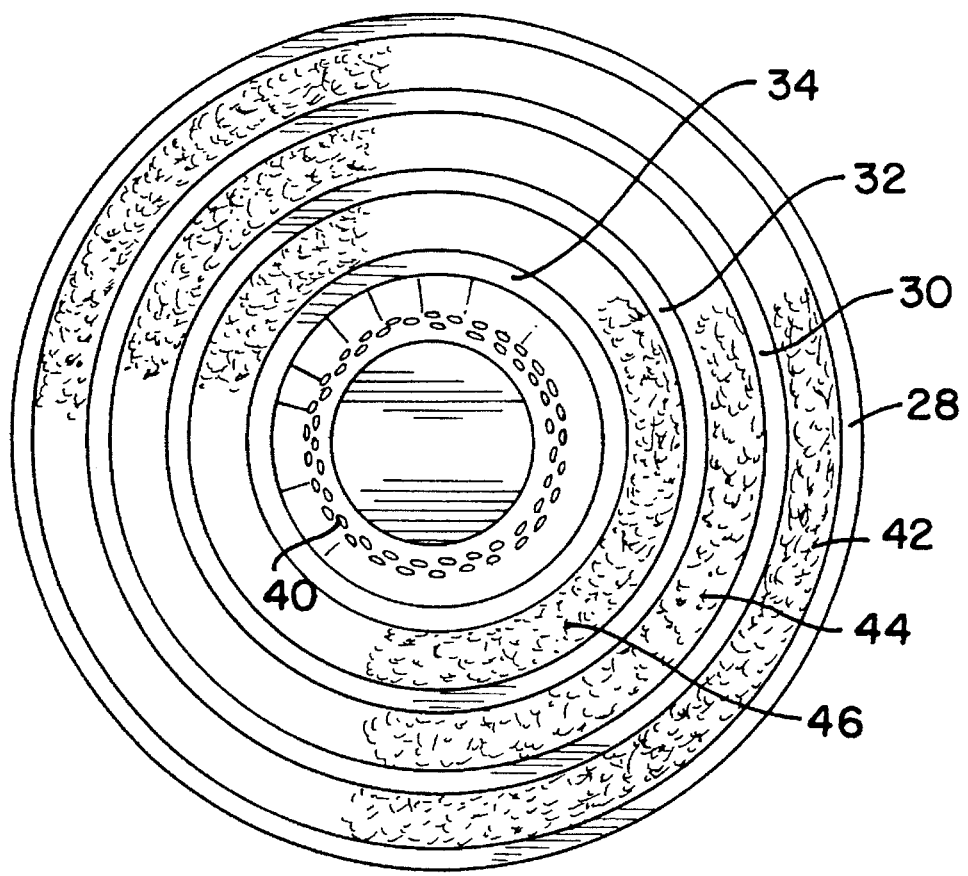
FIG. 2B is a top view of the specie of FIG. 2.

The specie of the invention illustrated in FIGS. 2A and 2B is comprised of a plurality of nested frustro-conically shaped cups 28, 30, 32 and 34 that can be made of terra cotta. All but the bottom cup 28 are provided with passageways extending through their walls that lie within bands such as 36, 38 and 40 that are spaced from the bottom and rim of the respective cup. The passageways can be cylindrical holes, formed, for example, by a laser beam, that are preferably between three and four millimeters in diameter so as to be large enough to permit microorganisms to flow through them.

The apparatus of FIGS. 2A and 2B can be used, for example, to make sauerkraut by placing shredded raw cabbage between the nested cups 28 and 30, 30 and 32 and 32 and 34 as indicated at 42, 44 and 46. A salt lactobacillus starter solution is added to the cabbage and downward pressure is applied to cups 30, 32 and 34 in any suitable manner. The bands 36 and 38 are not visible in FIG. 2B. As the cabbage ferments, the excess liquid [cabbage juices, salt solution, culture] passes through the successive bands of passageways 36, 38, and 40 leaving the sauerkraut behind.

Figure 3:
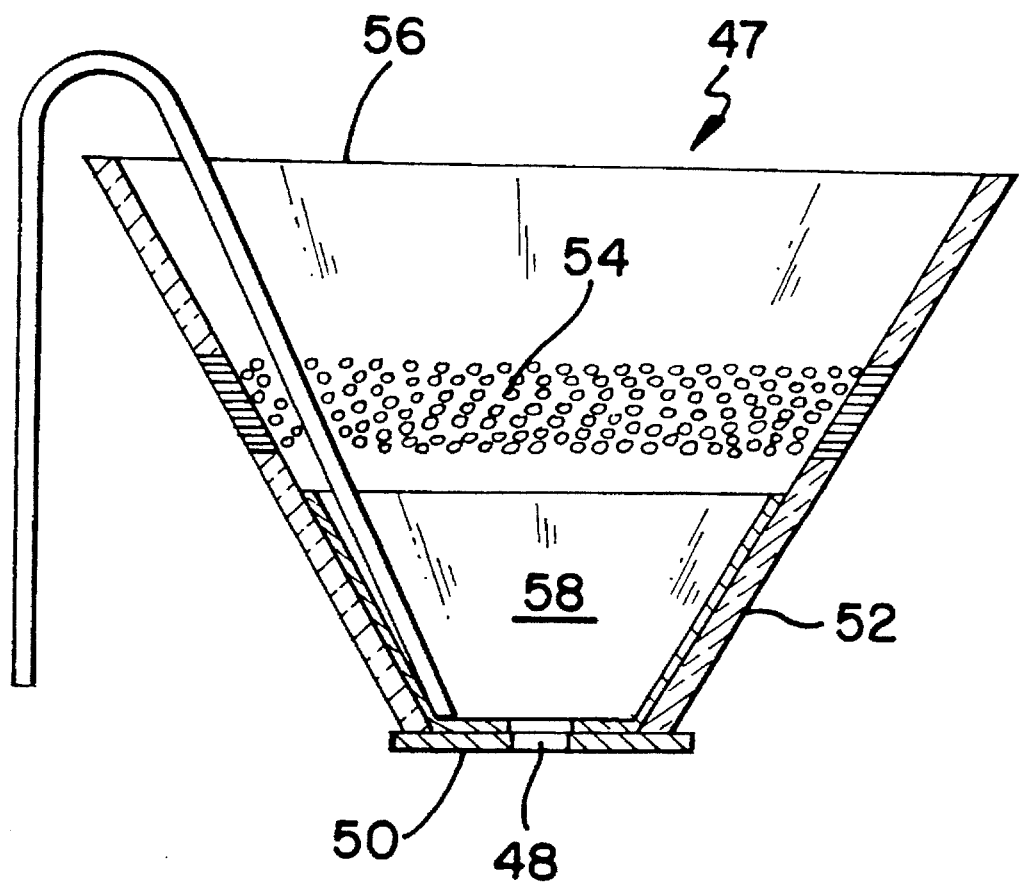
FIG. 3 is a cross-section of a specie of the invention in which cultures are grown in a single cup.

FIG. 3 illustrates another specie of the invention that is shown as being comprised of a single cup 47 that may in fact be a conical terra cotta flower pot having the usual opening 48 in the center of its flat bottom 50. The cup 47 need not be cylindrical. Passageways having a diameter of 2–4 millimeters are formed through the wall 52 of the cup 47 within a band 54 that is spaced from the bottom 50 and the rim 56. A plastic cup 58 fits snugly in the bottom of the cup 47 so as to prevent fluid from escaping through the hole 48, and a tube 60 is provided for introducing nutrient into the cup or for withdrawing fluid from it to any desired level.

What is claimed is:

1. Apparatus for growing colonies of microorganisms comprising:

an inert rigid member having two sides, one side for retaining microorganisms to be grown thereon and the other side for contacting a nutrient liquid;

means defining porous passageways extending from said one side to said other side of said rigid member; and said porous passageways being sized to enable capillary flow of the nutrient liquid therethrough to the microorganism and to preclude colonization therein by the microorganism.

2. Apparatus as set forth in claim 1 wherein said porous passageways have a maximum transverse dimension of 0.2 microns or less.

3. Apparatus for growing colonies of bacteria comprising:

an inert rigid member having two sides;

means defining porous passageways extending from one side to the other side of said rigid member;

means for bringing liquid, when present, into contact with one side of said inert member; and wherein said porous passageways have a maximum transverse dimension of 0.2 microns or less.

4. Apparatus as set forth in claim 1 wherein:

said rigid member is a plate;

said means for defining porous passageways are passageways extending from one side of said plate to the other; and including dish means for holding liquid in contact with one side of said member.

5. Apparatus for growing colonies of bacteria comprising:

an inert rigid plate member having two sides;

means defining porous passageways extending from one side to the other side of said rigid plate member;

a dish for holding liquid, when present, in contact with one side of said inert rigid plate member; and a sealed spacer of magnetic material located between said plate and the bottom of said dish.

6. Apparatus as set forth in claim 5 further comprising:

a magnetic handle adapted to pass magnetic flux through said plate and said spacer, whereby said plate and spacer may be lifted from said dish.

7. Apparatus for growing colonies of bacteria comprising:

an inert rigid member having two sides;

means defining porous passageways extending from one side to the other side of said rigid member; and means for holding liquid, when present, into contact with one side of said inert member; and wherein said inert rigid member is a cup having a wall and a bottom;

said means for defining porous passageways provides the passageways through the walls of said cup at a given distance from said bottom, said passageways having lateral dimensions between 2 and 4 millimeters; and said means for holding liquid in contact with one side of said member is a second cup having an interior that is larger than the exterior of said first cup whereby said first cup can nest in said second cup.

8. Apparatus for growing colonies of bacteria comprising:

an inert rigid member having two sides;

means defining porous passageways extending from one side to the other side of said rigid member; and means for holding liquid, when present, into contact with one side of said inert member; and wherein said rigid member is a ceramic cup having a wall and a bottom;

said means defining porous passageways is located on the wall of said cup and at a given distance from its bottom; and said means for holding liquid in contact with one side of said inert member is the cup itself.

9. Apparatus for growing colonies of microorganisms comprising:

a dish having a bottom;

a rigid plate having a first surface for contacting a nutrient liquid and a second surface for receiving microorganisms to be grown;

means defining capillary passageways extending between said first and second surfaces, said passageways being of such size as to prevent the microorganisms from entering them and to enable capillary flow of the nutrient liquid therethrough to the microorganism; and means for supporting said plate with said first surface facing and spaced from the bottom of said dish, whereby liquid of a given depth, when present in said dish, is in contact with said first surface.

10. Apparatus as set forth in claim 9 wherein the maximum lateral dimension of said passageways is equal to or less than 2 microns.

11. Apparatus as set forth in claim 9 wherein said means for supporting said plate rests on the bottom of said dish and is made of ferromagnetic material.

12. Apparatus for fermenting vegetable matter comprising:

a plurality of nested cups; and means defining passageways in all cups but the bottom one that are respectively spaced from their bottoms.

13. Apparatus for fermenting vegetable matter comprising:

a cup having a wall, a bottom and a rim;

means defining passageways extending through said wall within a band that is located between said bottom and said rim; and a tube adapted to be inserted into said cup.

14. Apparatus as set forth in claim 13 wherein said means defining passageways is located in a band between the bottom and top of a cup.

15. Apparatus as set forth in claim 13 wherein said passageways have lateral dimensions between 2 and 4 millimeters.

* * * * *